(12) United States Patent
Viart et al.

(10) Patent No.: US 6,682,562 B2
(45) Date of Patent: Jan. 27, 2004

(54) INTERVERTEBRAL DISC PROSTHESIS

(75) Inventors: Guy Viart, Saint Leger (FR); Frederic Marin, Paris (FR)

(73) Assignee: Eurosurgical SA, Beaurains (FR)

(*) Notice: Subject to any disclaimer, the term of this patent is extended or adjusted under 35 U.S.C. 154(b) by 0 days.

(21) Appl. No.: 10/220,424

(22) PCT Filed: Mar. 2, 2001

(86) PCT No.: PCT/FR01/00626
§ 371 (c)(1),
(2), (4) Date: Jan. 10, 2003

(87) PCT Pub. No.: WO01/68003
PCT Pub. Date: Sep. 20, 2001

(65) Prior Publication Data
US 2003/0191534 A1 Oct. 9, 2003

(30) Foreign Application Priority Data
Mar. 10, 2000 (FR) .............................. 00 03069

(51) Int. Cl.⁷ .................................................. A61F 2/44
(52) U.S. Cl. ..................................................... 623/17.14
(58) Field of Search ......................... 623/17.11, 17.12, 623/17.14, 17.15, 17.16

(56) References Cited
U.S. PATENT DOCUMENTS 5,401,269 A * 3/1995 Buttner-Janz et al. ........ 623/17
6,001,130 A * 12/1999 Bryan et al. ................... 623/17
6,063,121 A * 5/2000 Xavier et al. .................. 623/17
6,416,551 B1 * 7/2002 Keller ...................... 623/17.11
6,579,321 B1 * 6/2003 Gordon et al. ........... 623/17.16

FOREIGN PATENT DOCUMENTS

| DE | 22 63 842 | 7/1974 |
| EP | 0 176 728 | 4/1986 |
| EP | 0 560 141 | 9/1993 |
| FR | 2 694 882 | 2/1994 |

* cited by examiner

*Primary Examiner*—B E Snow
(74) *Attorney, Agent, or Firm*—Young & Thompson

(57) ABSTRACT

The invention concerns an intervertebral disc prosthesis comprising an upper plate (2) and a lower plate (3) anchored respectively on the upper end-plate and the lower end-plate of the vertebral bodies of the vertebrae lying above and below a spine, a central core (4) placed between the two plates (2, 3) which have an upper spherical cap (13) and a lower spherical cap (14) co-operating respectively with the spherical impressions (9) arranged in said upper and lower plates, and an annular element (5) made of viscoelastic material which is centred about the core (4) and is urged into contact with protuberances (12) provided on each internal surface (8) of the upper plate (2) and of the lower plate (3) so as to limit and control the bending, inclining and rotating movements of the upper plate (2) and of the lower plate (3) relative to each other and about the core (4), and ensure the positioning stability of the core (4) between the two plates (2, 3) and prevent fibrous deposits from penetrating inside the prosthesis (1).

11 Claims, 3 Drawing Sheets

INTERVERTEBRAL DISC PROSTHESIS

The present invention relates to an intervertebral disk prosthesis which is placed between the upper end plate and the lower end plate of the vertebral bodies of the overlying and underlying vertebrae of a spinal column.

German patent DE 2263842 discloses an intervertebral disk prosthesis comprising an upper plate and a lower plate which are provided respectively on their inner face with a cavity in the shape of a portion of a sphere and with a spherical core placed between the plates and collaborating with the cavities that have the same profile.

The upper plate and the lower plate are joined together and around the spherical core by a peripheral element made of a soft material such as plastic.

French patent FR 76 37174 (2 372 622) discloses an intervertebral disk prosthesis intended for all discal afflictions ensuing from crushing, displacement or deterioration of all kinds of vertebral bodies.

This disk prosthesis consists of a spherical element, forming a horizontal plate, which comprises semispherical sectors protruding from each side of the horizontal surface of the element.

The spherical sectors are placed at the center of the plate at equal distances from the anterior, posterior and lateral edges of the element.

The spherical element is placed between the upper end plate and the lower end plate of the vertebral bodies of the overlying and underlying vertebrae of the spinal column, so that the spherical sectors rest directly against said end plates of the vertebrae.

It is noted that the prosthesis described in patent FR 76 37174 has certain disadvantages regarding the bearing surface via which the spherical element bears against the upper end plate and the lower end plate of the vertebral bodies.

What happens is that the spherical sectors of the element bear directly against the bony end plates of the vertebral bodies, leading to these, on account of the spherical shape, digging into the bony end plates and making it possible for the prosthesis to work.

Patent EP 0 176 728 discloses an intervertebral disk prosthesis comprising an upper plate and a lower plate which are equipped respectively with a middle part with a concave profile intended to accommodate a bi-convex spacing piece with the same radius of curvature.

The spacing piece comprises a flat annular guide edge which is surrounded by an annular bulge which prevents said part from slipping or sliding out of the terminal plates.

It is noted that the intervertebral disk prosthesis described in patent EP 0 176 728 has certain disadvantages as regards operation of the articular connection between the spacer piece and the concave middle parts of each, upper and lower, plate. What happens is that this articular connection is not protected from the fibrous tissues surrounding the prosthesis, which may enter the latter and become fixed to the moving parts, impeding its correct operation.

The main function of the intervertebral disk prosthesis according to the present invention are:
- to restore the mobility between the overlying and underlying levels of the vertebrae of a spinal column using a two-ball or bi-concave connection,
- to restrict and control movements in bending, inclination and rotation of the upper plate and of the lower plate one with respect to the other and about the spacing piece or core,
- to prevent the fibrous tissues or the pseudo-synovial fibrous ganglion from attaching to the moving parts.

The intervertebral disk prosthesis according to the present invention comprises an upper plate and a lower plate which are anchored respectively to the upper end plate and the lower end plate of the vertebral bodies of the overlying and underlying vertebrae of a spinal column and a central core placed between the two plates which has an upper spherical cap and a lower spherical cap collaborating respectively with spherical cavities formed in said upper and lower plates, and an annular element made of a viscoelastic material which is centered around the core and which comes into contact with bosses provided on each inner face of the upper plate and of the lower plate so as to restrict and control the movements in bending, inclination and rotation of the upper plate and of the lower plate one with respect to the other and about the core, as to ensure stability in the positioning of the core between the two plates, and as to avoid fibrous deposits inside the prosthesis.

The intervertebral disk prosthesis according to the present invention comprises an upper plate and a lower plate which has an outer face integral with teeth to allow said plates to become anchored in the respective upper end plate and lower end plate of the vertebral bodies of the overlying and underlying vertebrae.

The intervertebral disk prosthesis according to the present invention has an inner face of the upper plate and of the lower plate which has a spherical cavity delimited by a circular rim which is raised with respect to the horizontal plane of the face.

The intervertebral disk prosthesis according to the present invention has an inner face which has, between the central cavity of spherical profile and the peripheral edge of each plate, bosses.

The intervertebral disk prosthesis according to the present invention has bosses which are arranged in an arc of a circle in such a way as to be centered about the spherical cavity.

The intervertebral disk prosthesis according to the present invention has a central core which has a peripheral ring arranged in a horizontal plane and which collaborates with an internal groove formed in the annular element.

The intervertebral disk prosthesis according to the present invention has an annular element which has a central opening for the passage of the caps of the central core and an internal groove opening into the central opening so as to accommodate the peripheral ring of said core when the disk prosthesis is being assembled.

The intervertebral disk prosthesis according to the present invention has an upper plate and a lower plate which are made of a cobalt/chromium alloy.

The intervertebral disk prosthesis according to the present invention has a central core which is made of a plastics material which has very good slip characteristics, such as polyethylene.

The intervertebral disk prosthesis according to the present invention has an annular element which is made of a viscoelastic material such as biocompatible elastomer for example.

The description which will follow with reference to the appended drawings which are given by way of nonlimiting examples will allow for a better understanding of the invention, of the characteristics it has and of the advantages it is likely to afford:

Figure 1:
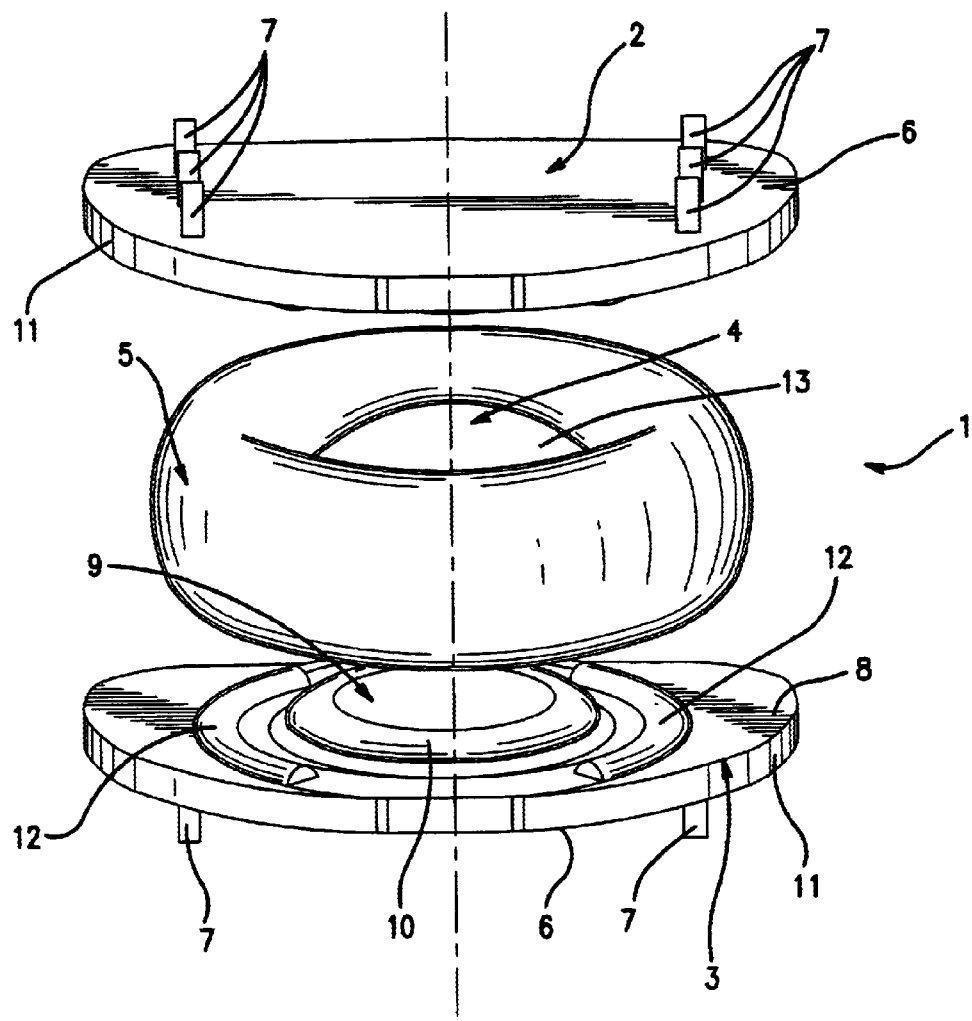
FIG. 1 is an exploded perspective view illustrating the intervertebral disk prosthesis according to the present invention.
Figure 2:
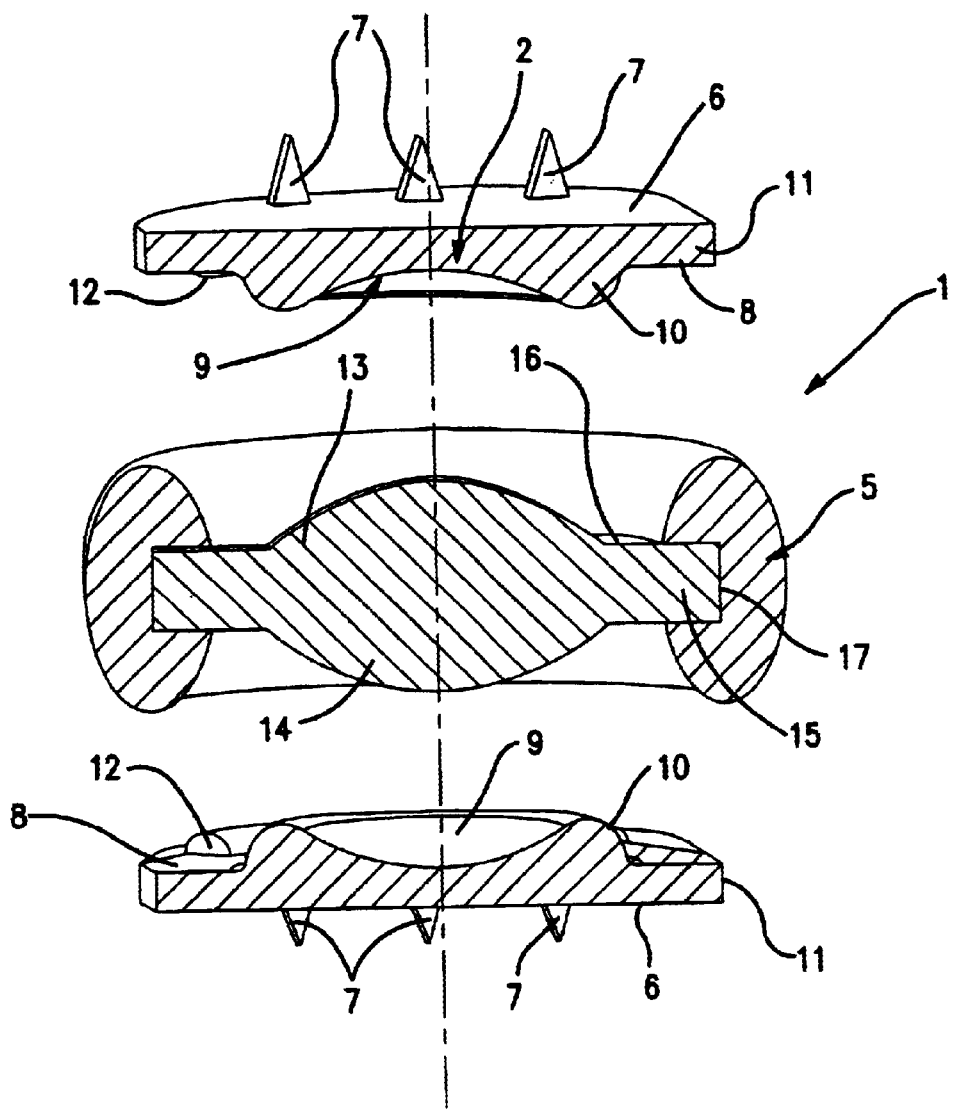
FIG. 2 is a view in section showing the intervertebral disk prosthesis according to the present invention.
Figure 3:
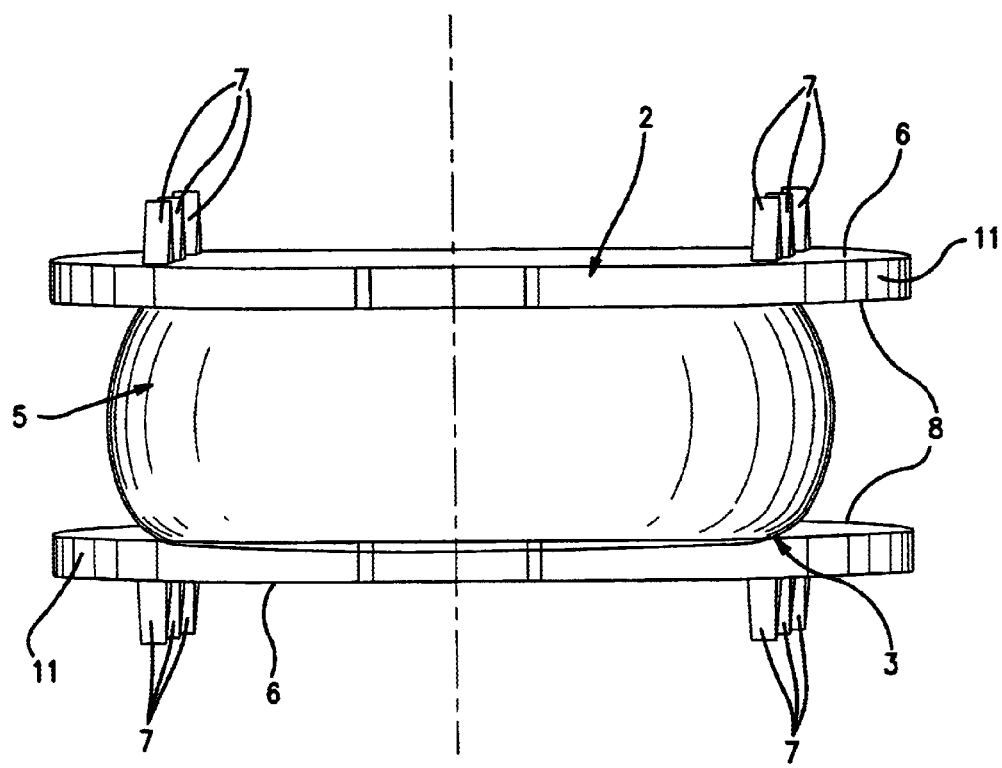
FIG. 3 is a view depicting the intervertebral disk prosthesis in the assembled position.

FIGS. 1 and 3 depict an intervertebral disk prosthesis 1 comprising two plates, an upper plate 2 and a lower plate 3, a central core 4 and an annular element 5, so as to restore mobility between the overlying and underlying levels of two adjacent vertebrae of a spinal column.

Each plate, upper 2 and lower 3, has an outer face 6 integral with teeth 7 to allow said plates to become anchored in, respectively, the upper and lower end plates of the vertebral bodies of the overlying and underlying vertebrae.

Each plate, upper 2 and lower 3, has, on the opposite side to its outer face 6, an inner face 6 which has a spherical cavity 9 delimited by a circular rim 10 which is raised with respect to the horizontal plane of the face 8.

The inner face 8 has, between the central cavity 9 of spherical profile and the peripheral edge 11 of each plate 2, 3 bosses 12 which are arranged on each side of said cavity.

The bosses 12 are arranged in an arc of a circle so as to be centered around the spherical cavity 9.

The upper plate 2 and the lower plate 3 have an outer profile in the shape of a "horseshoe", so as to best suit the profile of the vertebral end plates of the overlying and underlying vertebrae.

The particular shape of the upper plate 2 and of the lower plate 3 makes it possible to have the greatest possible area of contact with the corresponding vertebra, so as to avoid said plates digging into the body of the vertebra.

The upper plate 2 and the lower plate 3 are made of a cobalt/chromium alloy.

The central core 4 has an upper spherical cap 13 and a lower spherical cap 14 which respectively collaborate with the cavities 9, of the same profile, of each, upper 2 and lower 3, plate.

The central core 4 has a peripheral ring 15 arranged in a horizontal plane and allowing the rotation of said core with respect to the upper plate 2 and the lower plate 3 to be restricted.

Thus, the disk prosthesis 1 comprises an articular connection of the ball-joint type because of the profile of the caps 13 and 14 of the central core 4 which collaborate with the cavities 9 of each, upper 2 and lower 3, plate.

It may be noted that the articular connection of the ball-joint type of the disk prosthesis 1 constitutes a connection with 5 degrees of freedom between the upper plate 2 and the lower plate 3, namely:

3 rotations, 2 translations.

The central core 4 is made of a plastic with good slip characteristics, such as polyethylene.

It may be noted that the central core 4 originates from a set of cores the size of which varies according to the thickness of the peripheral ring 15. The central core 4 is selected on the basis of the dimensions of the opening made by the surgeon between the upper end plate and the lower end plate of the overlying and underlying vertebral bodies so that the intervertebral prosthesis is perfectly matched to the height of this opening.

The annular element 5 has a central opening 16 the inside diameter of which slightly exceeds that of each cap 13, 14 of the central core 4 at the point where said caps and the peripheral ring 15 meet.

The annular element 5 has an internal groove 17 opening into the central opening 16 so as to accommodate the peripheral ring 15 of the central core 4 when the disk prosthesis 1 is being assembled.

The annular element 5 is made of a viscoelastic material such as biocompatible elastomer for example.

It may be seen, when the disk prosthesis 1 is being assembled, that the annular element 5 comes into contact with the upper plate 2 and the lower plate 3 at the bosses 12 provided on each inner face 8, while the spherical caps 13 and 14 of the central core 4 are also in contact with the cavities 9 in each plate.

It can be seen that the control and restriction of movements in bending, extension and lateral inclination of the disk prosthesis 1 is obtained by the compression of the annular element 5 by the upper plate 2 and the lower plate 3 when they are anchored between the upper end plate and the lower end plate of the overlying and underlying vertebral bodies of a spinal column.

Thus, this restriction and control of movements in bending, extension and lateral inclination of the disk prosthesis 1 is dependent upon the height of the bosses made on the inner faces 8 of the upper plate 2 and of the lower plate 3 of the prosthesis.

As far as control and restriction in terms of axial rotation of the disk prosthesis 1 is concerned, this is obtained by the friction of the annular element 5 on the upper plate 2 and the lower plate 3, and by the obstacle of the annular element 5 on the bosses 12 in an arc of a circle which are provided on the inner faces 8 of each plate.

It may be noted that the annular element makes it possible to prevent fibrous tissues or the pseudo-synovial fibrous ganglion from attaching to the moving parts of the disk prosthesis 1, given that it lies between the upper plate 2 and the lower plate 3.

In addition, the central core 4 is connected to the annular element 5 and the element is trapped between the two plates 2 and 3 so as to ensure stability in the positioning of the core between the two plates through the return action of the annular element.

It must also be understood that the foregoing description has been given merely by way of example and that it does not in any way restrict the field of the invention which would not be overstepped if the embodiment details described were to be replaced will any other equivalent.

What is claimed is:

1. An intervertebral disk prosthesis comprising an upper plate (2) and a lower plate (3) which are adopted to be anchored respectively to the upper end plate and the lower end plate of the vertebral bodies of the overlying and underlying vertebrae of a spinal column and a central core (4) placed between the two plates (2, 3) which has an upper spherical cap (13) and a lower spherical cap (14) collaborating respectively with spherical cavities (9) formed in said upper and lower plates, said disk further comprising an annular element (5) made of a viscoelastic material which is centered around the core (4) and which comes into contact with bosses (12) provided on a inner face (8) of the upper plate (2) and of the lower plate (3) so as to restrict and control the movements in bending, inclination and rotation of the upper plate (2) and of the lower plate (3) one with respect to the other and about the core (4), as to ensure stability in the positioning of the core (4) between the two plates (2, 3), and as to avoid fibrous deposits inside the prosthesis (1).

2. The intervertebral disk prosthesis as claimed in claim 1, characterized in that each plate, the upper plate (2) and the lower plate (3), has an outer face (6) integral with teeth (7) to allow said plates to become anchored in the respective upper end plate and lower end plate of the vertebral bodies of the overlying and underlying vertebrae.

3. The intervertebral disk prosthesis as claimed in claim 1, characterized in that the inner face (8) of the upper plate (2) and the lower plate (3) has a spherical cavity (9) delimited by a circular rim (10) which is raised with respect to the horizontal plane of the face (8).

4. The intervertebral disk prosthesis as claimed in claim 1, characterized in that the inner face (8) has, between the central cavity (9) of spherical profile and a peripheral edge (11) of each plate (2, 3), bosses (12).

5. The intervertebral disk prosthesis as claimed in claim 1, characterized in that the bosses (12) are arranged in an arc of a circle in such a way as to be centered about the spherical cavity (9).

6. The intervertebral disk prosthesis as claimed in claim 1, characterized in that the central core (4) has a peripheral ring (15) arranged in a horizontal plane and which collaborates with an internal groove (17) formed in the annular element (5).

7. The intervertebral disk prosthesis as claimed in claim 1, characterized in that the annular element (5) has a central opening (16) for the passage of the caps (13, 14) of the central core (4) and an internal groove (17) opening into the central opening (16) so as to accommodate the peripheral ring (15) of said core when the disk prosthesis (1) is being assembled.

8. The intervertebral disk prosthesis as claimed in claim 1, characterized in that the upper plate (2) and the lower plate (3) are made of a cobalt/chromium alloy.

9. The intervertebral disk prosthesis as claimed in claim 1, characterized in that the central core (4) is made of a plastic which has very good slip characteristics.

10. The intervertebral disk prosthesis as claimed in claim 9, wherein the plastic is polyethylene.

11. The intervertebral disk prosthesis as claimed in claim 1, characterized in that the annular element (5) is made of a viscoelastic material is a biocompatible elastomer.

* * * * *